United States Patent [19]

Jacobsen et al.

[11] Patent Number: 5,800,454
[45] Date of Patent: Sep. 1, 1998

[54] CATHETER DELIVERABLE COILED WIRE THROMBOGINIC APPARATUS AND METHOD

[75] Inventors: Stephen C. Jacobsen; Clark C. Davis, both of Salt Lake City; John A. Lippert, Park City, all of Utah

[73] Assignee: Sarcos, Inc., Salt Lake City, Utah

[21] Appl. No.: 818,268

[22] Filed: Mar. 17, 1997

[51] Int. Cl.[6] ................................... A61M 29/00
[52] U.S. Cl. .................... 606/191; 606/194; 606/198; 606/200
[58] Field of Search ............... 606/191, 198, 606/200, 194; 604/104

[56] References Cited

U.S. PATENT DOCUMENTS

| | | |
|---|---|---|
| 4,994,069 | 2/1991 | Ritchart et al. |
| 5,217,484 | 6/1993 | Marks .................... 606/200 |
| 5,582,619 | 12/1996 | Ken ........................ 606/191 |
| 5,639,277 | 6/1997 | Mariant et al. ......... 606/191 |
| 5,649,949 | 7/1997 | Wallace et al. ........ 606/191 |

*Primary Examiner*—Michael Powell Buiz
*Assistant Examiner*—Julian W. Woo
*Attorney, Agent, or Firm*—Thorpe, North & Western, LLP

[57] ABSTRACT

A catheter deliverable thrombogenic device includes a catheter for threading into a body vasculature passageway to a target location, and a resilient wire element coiled and shaped to occupy a certain volume when unconstrained, and to straighten when inserted lengthwise into and constrained by the catheter, for ultimate discharge therefrom to expand and occupy the target location. The wire element includes a first length of wire, and a second length of wire coiled about the first wire to form a composite pair. The composite pair itself is coiled and shaped to occupy the certain volume when unconstrained, and to straighten when inserted lengthwise into and constrained by the catheter.

19 Claims, 1 Drawing Sheet

CATHETER DELIVERABLE COILED WIRE THROMBOGINIC APPARATUS AND METHOD

BACKGROUND OF THE INVENTION

This invention relates to vaso-occlusive devices for arresting blood flow in body vasculature or cavities.

Devices which occlude blood flow and/or initiate blood clotting, and which can be introduced into the body via a catheter or other cannula are valuable for stopping bleeding or the threat of bleeding, cutting off blood supply to a diseased organ, reducing blood flow to an organ, rebuilding a defective organ, etc. Devices typically utilized are coils or particles which are deployed through a catheter to a target site where arresting blood flow is desired. In addition, various solutions may be delivered through the catheter either for assisting and accelerating clotting or in treating the medical problem.

Typical devices used in the past include platinum coils which were inserted into the catheters and then pushed therethrough to the target site using a conventional catheter guide wire or other device as a "plunger". The coil devices are preset in a desired shape, typically a simple helix, so that after they are delivered to the desired site, they resume their original shape. Prior art platinum coil devices have often been ineffective in holding their positions at the delivered site, and thus ineffective in occluding at the site.

Types of particles used in the past for occluding blood flow include PVA or hydrophilic particles that swell to a larger size when blood is absorbed. This swelling, of course, aids in stopping the flow of blood, assuming the positions of the particles are maintained.

The prior art approaches for arresting blood flow are fairly rudimentary and only partially successful in achieving the desired blood flow stoppage.

SUMMARY OF THE INVENTION

It is an object of the invention to provide new and improved vaso-occlusive type devices which may be easily deployed to a target site in the human body and which are effective in inducing clotting or otherwise arresting blood flow.

It is also an object of the invention to provide such devices which are easily manufactured and which can be tailor-made in size and configuration to accommodate the targeted deployment location.

It is a further object of the invention to provide such devices which may be quickly and easily deployed to a target location in the body, and remain in place.

The above and other objects of the invention are realized in a specific illustrative embodiment of a thrombogenic apparatus which includes a catheter for threading into a body vasculature passageway to a target location, and a wire element coiled and shaped to occupy a certain volume when unconstrained, and to straighten when inserted lengthwise into and constrained by the catheter, for ultimate discharge therefrom to expand and occupy the target location.

In accordance with one aspect of the invention, the wire element is formed to have a coil diameter which becomes gradually smaller toward a distal end. In accordance with another aspect of the invention, the smaller diameter coils near and at the distal end are tightly wound to inhibit flow of blood therepast, when inserted into a blood vessel.

The wire element advantageously is a pair of wires, one coiled about the other and then the composite pair formed into the larger coil.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1A:
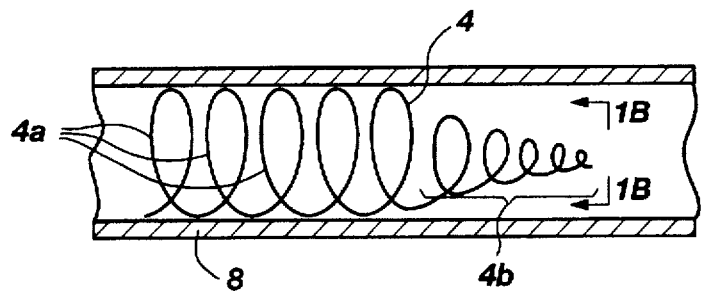
FIG. 1A is a side, fragmented, cross-sectional view of a thrombogenic, coiled-wire device made in accordance with the principles of the present invention.
Figure 1B:
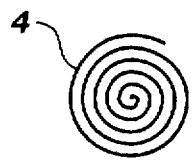
FIG. 1B is a front end view of the wire coil of FIG. 1A, taken along lines 1B—1B.

Referring to FIG. 1A and 1B, there is shown a side, cross-sectional, fragmented view and an end view respectively of a resilient wire 4 which has been formed into a coil. In FIG. 1A, the wire 4 is shown disposed in a blood vessel 8. The wire 4 includes a larger diameter section 4a and a gradually narrowing section 4b. The coils in the larger diameter section 4a expand to contact the walls of the blood vessel 8 to hold the coil wire 4 in place. The narrower diameter section 4b serves as the leading or distal end of the coil wire 4, facilitates orienting the device in the vessel, and preferably is more flexible to minimize damage or trauma to vessel walls when inserting the coil wire (to be discussed momentarily).

The wire 4 might, for example, be formed of a highly elastic nickel-titanium alloy wire. The diameter of the larger coil diameter section 4a advantageously is from about 3 to 12 mm, whereas the diameter of the smallest diameter coil in section 4b advantageously is from about 0.75 to 2 mm, both calculated when the coil wire 4 is unconstrained.

Tapering the diameter of the wire coil 4 as in section 4b provides a greater barrier and density to the flow of blood, and thus greater ability to occlude, as best seen in the FIG. 1B view, taken along lines 1B—1B of FIG. 1A. (Controlling the tapering of and spacing between coils, by varying flexibility of the wire, allows use of the coil as a limited leak valve or a complete block.)

Figure 2:
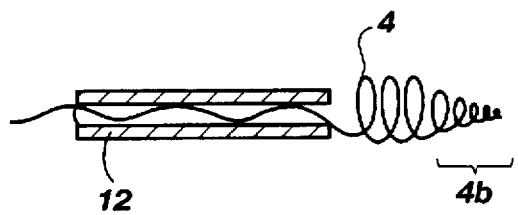
FIG. 2 is a side, fragmented, cross-sectional view of a coil-wire device made in accordance with the principles of the present invention, shown partially disposed in a catheter.

FIG. 2 shows a side, fragmented, cross-sectional view of a wire coil 4 partially disposed in a catheter 12. For deployment of the coil wire 4 to a target location in a vasculature passageway or other cavity in the body, the wire 4 may be threaded into the catheter 12 generally straight as shown in FIG. 2, and then pushed through the catheter by another guide wire (not shown) or similar device which serves as a type of plunger to force the coil wire out the distal end of the catheter where it then expands to seat itself at the target location. When deployed to a target site in the body past which blood is flowing, the wire coil 4 serves to slow the flow to allow for coagulation or clotting and ultimately the arresting of further flow. To aid in the clotting process, clotting agents, in the form of a solution, might be delivered through the catheter 12 along with the deployment of the coil wire 4, to the target site. In addition, fibrous material attached to the coils would also assist in promotion of clotting.

The embodiment of the wire coil 4 shown in FIG. 2 includes a narrowed distal section 4b in which the coils are tightly wound to the extent that the adjacent coils touch. With such high density packing of the coils, the flow of blood is substantially stopped even before coagulation or clotting takes place.

Figure 3A:
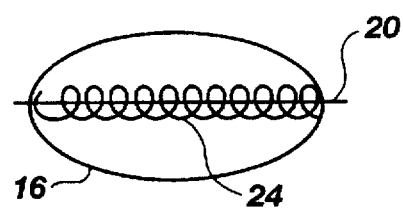
FIG. 3A is a side, fragmented view of a segment of a composite pair of wires which would be formed into a coiled wire device shown in FIG. 3B, in accordance with the principles of the present invention.
Figure 3B:
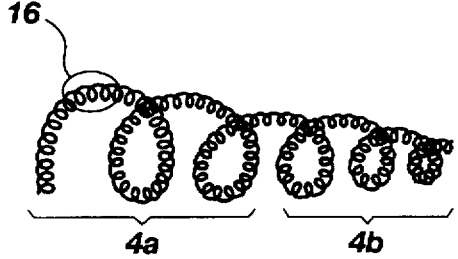
FIG. 3B is a side, fragmented view of the composite pair of wires of FIG. 3A formed into a coiled-wire device of the present invention.

FIGS. 3A and 3B show another embodiment of the present invention to include a central wire 20 and an outer wire 24 coiled (primary coil) about the central wire. This composite pair of wires is then formed into a larger coil (secondary coil), shown in FIG. 3B, which includes a generally cylindrical portion 4a and a tapered portion 4b, similar to that shown in FIG. 1A. To obtain greater flexibility for the distal or tapered section 4b of the composite pair, the central wire 20 could itself be tapered (or gradually reduced in diameter) to a narrower diameter in section 4b or could be tapered toward its end, but short of the end. The narrower diameter, of course, would allow greater flexibility and the degree of flexibility could be controlled by controlling the diameter of the central wire 20.

An alternative to tapering the central wire 20 is to provide a central wire (either solid or tubular), formed with cuts appropriately spaced and sized to obtain the flexibility desired.

Advantageously, the diameter of the coil 24 is from about 0.001 inch to 0.005 inch. The central wire 20 could be made of nickel-titanium alloy, stainless steel or other suitable alloy or substitute.

Figure 4:
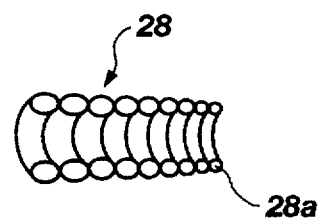
FIG. 4 is a side, fragmented view of a section of another embodiment of a coiled-wire device made in accordance with the present invention.

FIG. 4 shows a side, fragmented view of still another embodiment of the thrombogenic device of the present invention. This embodiment involves a tightly coiled wire 28 (primary coil) which, itself, is formed into a larger coil (secondary coil) similar to that shown in FIG. 3B, but without the central wire. In order to achieve variable flexibility of the larger coil, the diameter of the wire 28 could be varied so that the smaller diameter sections of the wire would have greater flexibility than the larger diameter sections. In FIG. 4, the diameter of the wire 28 becomes gradually smaller toward a distal end 28a. In forming the tightly wound coil wire 28 of FIG. 4 into a larger coil such as shown in FIG. 3B, that part of the coil wire 28 having the narrower diameter would be located at the distal end or section (4b of FIG. 32B).

Of course, the coil wire 28, of FIG. 4, could be provided with a central wire, similar to the FIG. 3A embodiment, which could be suitably tapered, along with the tapering of the wire 28, to control flexibility along the length of the combination.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. Thrombogenic apparatus comprising
a catheter for threading into a body vasculature passageway to a target location, and
a resilient wire means coiled and shaped to occupy a certain volume when unconstrained, and to straighten when inserted lengthwise into and constrained by the catheter, for ultimate discharge therefrom to expand and occupy the target location, said wire means further including
a first length of wire, and
a second length of wire coiled into a primary coil about the first wire to form a composite pair, said composite pair itself being coiled into a secondary coil and shaped to occupy said volume when unconstrained, and to straighten when inserted lengthwise into and constrained by the catheter.

2. An apparatus as in claim 1 wherein said first wire is tapered to be narrower at a distal end, and thus more flexible at the distal end.

3. An apparatus as in claim 1 or 2 wherein said second wire is tapered to be narrower at a distal end, and thus more flexible at the distal end.

4. An apparatus as in claim 1 wherein said first wire extends to a location short of a distal end of the second coiled wire so that a distal end of the composite pair is more flexible than other portions of the composite pair.

5. An apparatus as in claim 1 wherein said first wire includes a plurality of cuts at selected locations along at least a portion of the length to increase the flexibility thereof.

6. An apparatus as in claim 1 wherein said composite pair is formed to have a coil diameter which becomes gradually smaller toward the distal end.

7. An apparatus as in claim 6 wherein the smaller diameter coils near and at the distal end are tightly wound to inhibit flow of blood therepast when inserted in a blood vessel.

8. Thrombogenic apparatus comprising
a catheter for threading into a body vasculature passageway to a target location,
a resilient wire means coiled and shaped to occupy a certain volume when unconstrained, and to straighten when inserted lengthwise into and constrained by the catheter, for ultimate discharge therefrom to expand and occupy the target location, said wire means comprising a tightly coiled length of wire which itself is formed into a larger coil and shaped to occupy said volume when unconstrained, and to straighten when inserted lengthwise into and constrained by the catheter, the diameter of the wire becoming gradually smaller toward a distal end, and therefore more flexible, and
a core wire disposed to extend centrally in the coil formed by the wire means.

9. An apparatus as in claim 8 wherein the diameter of the larger coil becomes smaller toward a distal end.

10. An apparatus as in claim 8 wherein said wire means is made of a material selected from the group consisting of an alloy of nickel and titanium, and stainless steel.

11. Apparatus as in claim 8 wherein said wire means is solid.

12. Apparatus as in claim 8 wherein said wire means is tubular having sidewalls surrounding a central hollow.

13. Apparatus as in claim 8 wherein the diameter of the core wire is selectively varied to thereby selectively vary the flexibility of the combination wire means and core wire.

14. Thrombogenic apparatus comprising
a catheter for threading into a body vasculature passageway to a target location,
a resilient wire means comprising a length of wire coiled into a primary coil which, itself, is coiled into a larger secondary coil, and shaped to occupy a certain volume when unconstrained and to straighten when inserted lengthwise into and constrained by the catheter, said wire means being formed to be more flexible at one end than the other.

15. Thrombogenic apparatus comprising a catheter for threading into a body vasculature passageway to a target location, and a resilient wire means coiled and shaped to occupy a certain volume when unconstrained, and to straighten when inserted lengthwise into and constrained by the catheter, for ultimate discharge therefrom to expand and occupy the target location, said wire means further including a first length of wire, and a second length of wire coiled about the first wire to form a composite pair, said second wire being tapered to be narrower at a distal end, and thus more flexible at the distal end, said composite pair itself being coiled and shaped to occupy said volume when unconstrained, and to straighten when inserted lengthwise into and constrained by the catheter.

16. Thrombogenic apparatus comprising a catheter for threading into a body vasculature passageway to a target location, and a resilient wire means coiled and shaped to occupy a certain volume when unconstrained, and to straighten when inserted lengthwise into and constrained by the catheter, for ultimate discharge therefrom to expand and occupy the target location, said wire means further including a first length of wire, and a second length of wire coiled about the first wire to form a composite pair, said first wire extending to a location short of a distal end of the second coiled wire so that a distal end of the composite pair is more flexible than other portions of the composite pair, said composite pair itself being coiled and shaped to occupy said volume when unconstrained, and to straighten when inserted lengthwise into and constrained by the catheter.

17. Thrombogenic apparatus comprising a catheter for threading into a body vasculature passageway to a target location, and a resilient wire means coiled and shaped to occupy a certain volume when unconstrained, and to straighten when inserted lengthwise into and constrained by the catheter, for ultimate discharge therefrom to expand and occupy the target location, said wire means further including a first length of wire including a plurality of cuts at selected locations along at least a portion of the length to increase the flexibility thereof, and a second length of wire coiled about the first wire to form a composite pair, said composite pair itself being coiled and shaped to occupy said volume when unconstrained, and to straighten when inserted lengthwise into and constrained by the catheter.

18. Thrombogenic apparatus comprising a catheter for threading into a body vasculature passageway to a target location, and a resilient wire means coiled and shaped to occupy a certain volume when unconstrained, and to straighten when inserted lengthwise into and constrained by the catheter, for ultimate discharge therefrom to expand and occupy the target location, said wire means further including a first length of wire including a plurality of cuts at selected locations along at least a portion of the length to increase the flexibility thereof, and a second length of wire coiled about the first wire to form a composite pair, said composite pair itself being coiled and shaped to occupy said volume when unconstrained, and to straighten when inserted lengthwise into and constrained by the catheter, said composite pair being formed to have a coil diameter which becomes gradually smaller toward the distal end, the smaller diameter coils near and at the distal end being tightly wound to inhibit flow of blood therepast when inserted in a blood vessel.

19. Thrombogenic apparatus comprising a catheter for threading into a body vasculature passageway to a target location, and a resilient tubular wire means having sidewalls surrounding a central hollow and being coiled and shaped to occupy a certain volume when unconstrained, and to straighten when inserted lengthwise into and constrained by the catheter, for ultimate discharge therefrom to expand and occupy the target location, said wire means comprising a tightly coiled length of wire which itself is formed into a larger coil and shaped to occupy said volume when unconstrained, and to straighten when inserted lengthwise into and constrained by the catheter, the diameter of the wire becoming gradually smaller toward a distal end, and therefore more flexible.

* * * * *